(12) United States Patent
Akins

(10) Patent No.: US 8,239,003 B2
(45) Date of Patent: Aug. 7, 2012

(54) SYSTEM AND METHOD OF INTEGRATING ELECTROMAGNETIC MICROSENSORS IN GUIDEWIRES

(75) Inventor: Samuel Joseph Akins, Tewksbury, MA (US)

(73) Assignee: General Electric Company, Schenectady, NY (US)

( * ) Notice: Subject to any disclaimer, the term of this patent is extended or adjusted under 35 U.S.C. 154(b) by 1265 days.

(21) Appl. No.: 11/735,634

(22) Filed: Apr. 16, 2007

(65) Prior Publication Data

US 2008/0255446 A1    Oct. 16, 2008

(51) Int. Cl.
*A61B 5/05* (2006.01)

(52) U.S. Cl. ........ 600/424; 600/433; 600/434; 600/435; 600/585; 604/523

(58) Field of Classification Search ................ 600/424, 600/433–435, 585; 604/523–529
See application file for complete search history.

(56) References Cited

U.S. PATENT DOCUMENTS

| | | | |
|---|---|---|---|
| 4,173,228 A | 11/1979 | Van Steenwyk et al. | |
| 4,572,198 A | 2/1986 | Codrington | |
| 4,719,924 A | 1/1988 | Crittenden et al. | |
| 4,763,647 A | 8/1988 | Gambale | |
| 4,832,047 A | 5/1989 | Sepetka et al. | |
| 4,905,698 A | 3/1990 | Strohl, Jr. et al. | |
| 5,386,828 A | 2/1995 | Owens et al. | |
| 5,402,799 A | 4/1995 | Colon et al. | |
| 5,406,960 A | 4/1995 | Corso, Jr. | |
| 5,497,786 A | 3/1996 | Urick | |
| 5,727,553 A | 3/1998 | Saad | |
| 5,876,386 A | 3/1999 | Samson | |
| 6,226,547 B1 | 5/2001 | Lockhart et al. | |
| 6,233,476 B1 | 5/2001 | Strommer et al. | |
| 6,615,155 B2 | 9/2003 | Gilboa | |
| 6,785,571 B2 | 8/2004 | Glossop | |
| 6,947,788 B2 | 9/2005 | Gilboa et al. | |
| 7,169,161 B2 | 1/2007 | Bonnette et al. | |
| 7,286,868 B2 * | 10/2007 | Govari | 600/424 |
| 2002/0042571 A1 | 4/2002 | Gilboa et al. | |
| 2002/0198676 A1 | 12/2002 | Kirsch et al. | |
| 2004/0097804 A1 | 5/2004 | Sobe | |
| 2004/0181174 A2 | 9/2004 | Davis et al. | |
| 2005/0240147 A1 | 10/2005 | Makower et al. | |
| 2005/0283067 A1 | 12/2005 | Sobe | |
| 2006/0173291 A1 | 8/2006 | Glossop | |
| 2006/0189896 A1 * | 8/2006 | Davis et al. | 600/585 |
| 2006/0241519 A1 | 10/2006 | Hojeibane et al. | |
| 2007/0027524 A1 | 2/2007 | Johnson et al. | |
| 2007/0208252 A1 * | 9/2007 | Makower | 600/424 |

* cited by examiner

*Primary Examiner* — Brian Casler
*Assistant Examiner* — Daniel Huntley
(74) *Attorney, Agent, or Firm* — Kenneth E. Horton; Kirton McConkie PC

(57) ABSTRACT

A system and method of integrating electromagnetic microsensors into interventional endovascular devices such as guidewires for tracking guidewires within vessels of the body with the use of a surgical navigation system.

28 Claims, 8 Drawing Sheets

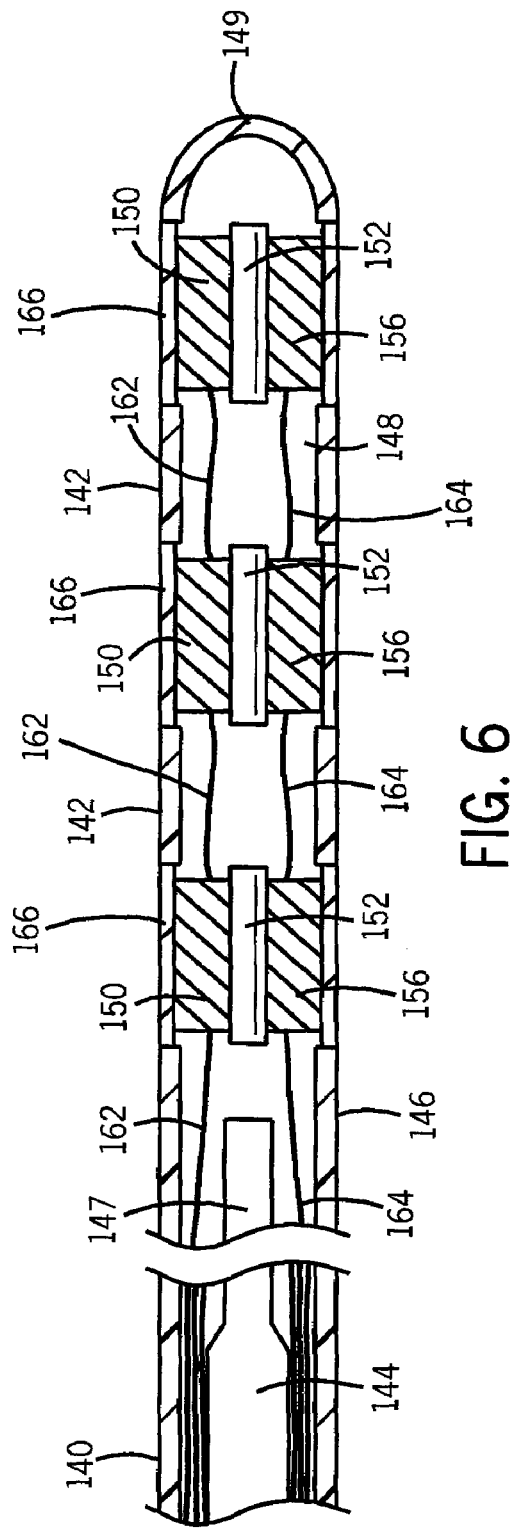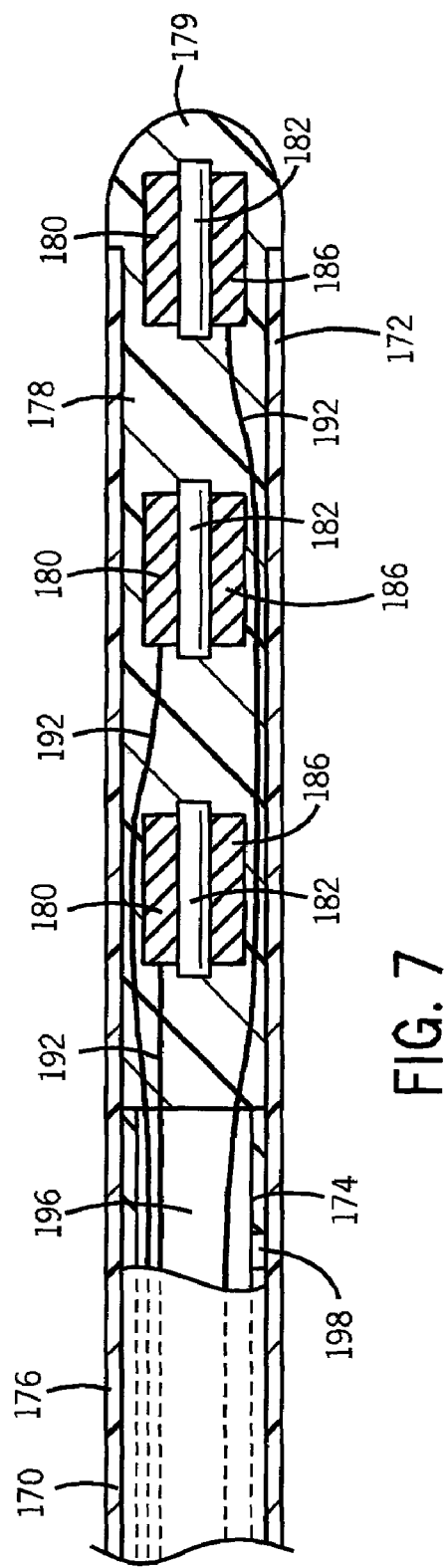

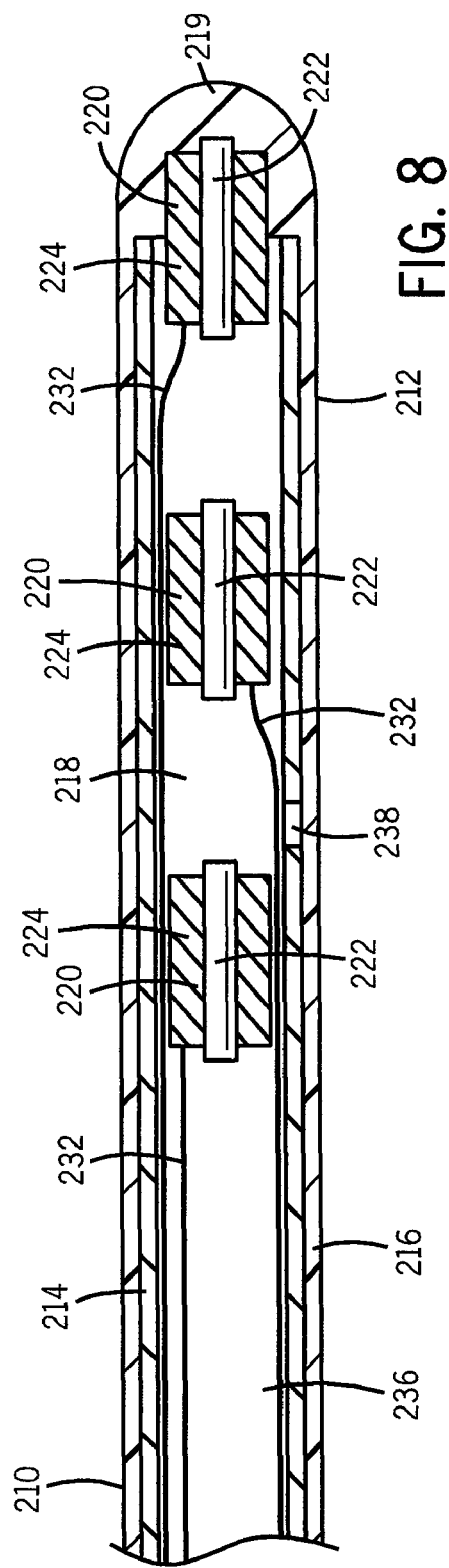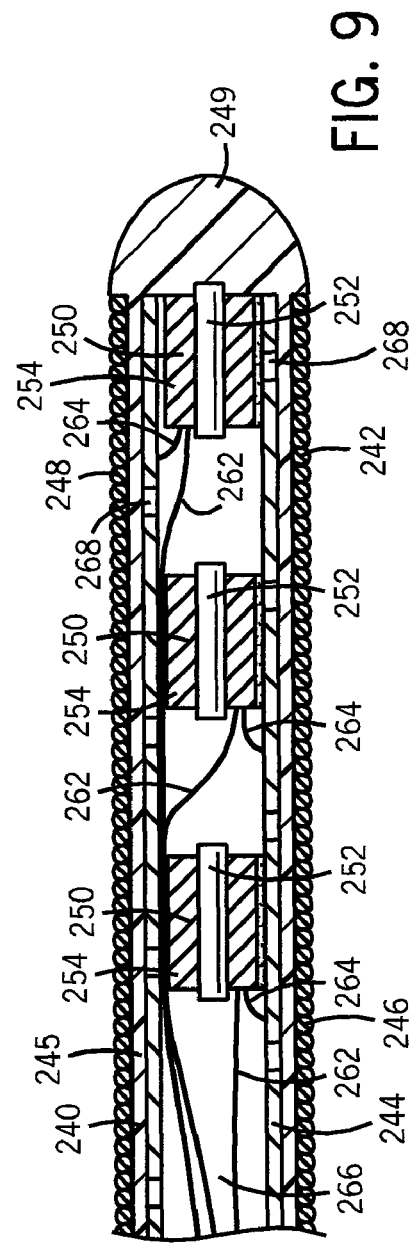

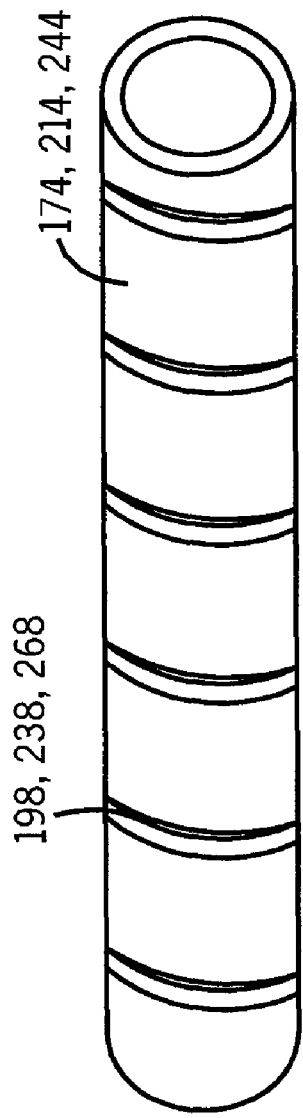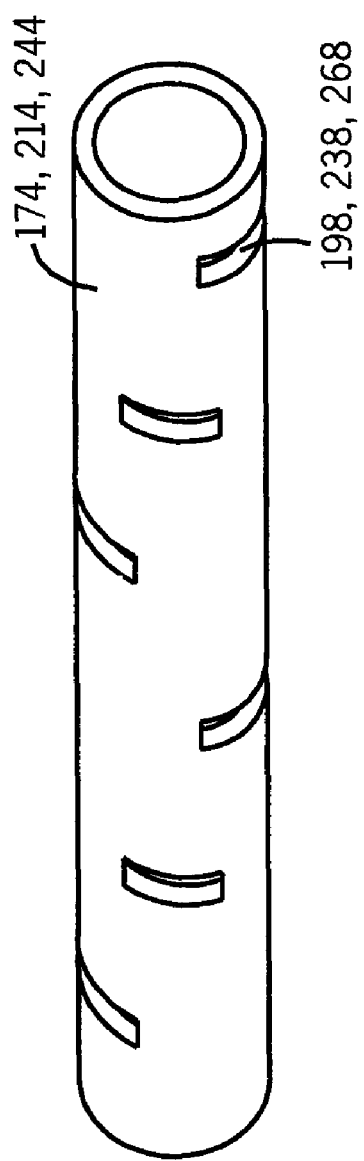

SYSTEM AND METHOD OF INTEGRATING ELECTROMAGNETIC MICROSENSORS IN GUIDEWIRES

BACKGROUND OF THE INVENTION

This disclosure relates generally to guidewires, and more particularly, to a system and method of integrating electromagnetic microsensors into interventional endovascular devices (guidewires) for tracking the guidewires within vessels of the body with a surgical navigation system.

Guidewires are used in the body, particularly the vascular system in endovascular applications. Guidewires are used to aid in the insertion of catheters into the body and to evaluate the vessel along which the catheter will travel. In general, a guidewire is inserted into a body system such as the vascular system at the point of entry, which is usually a small percutaneous incision in the arm, leg or groin, and advanced through the lumen in one or more blood vessels to the target site. A generally hollow cylindrical catheter is slipped over the guidewire and directed to the target site by following the guidewire. The catheter doesn't have the stiffness or rigidity of the guidewire. The guidewire and catheter must be precisely and efficiently positioned at a predetermined location within the blood vessel in order to most effectively treat the underlying medical condition.

Surgical navigation systems track the precise location of surgical instruments in relation to multidimensional images of a patient's anatomy. Additionally, surgical navigation systems use visualization instruments to provide the surgeon with co-registered views of these surgical instruments with the patient's anatomy. Surgical navigation systems may be based on any known tracking technology such as, for example, electromagnetic tracking technology. The surgical navigation system determines the position and/or orientation of a microsensor within a surgical instrument (e.g., a guidewire or a catheter) and conveys this location to a user. The position and orientation information can be conveyed by virtually superimposing a graphic representation of a portion of the surgical instrument onto a patient image. The surgical instrument can be viewed in real-time or near real-time as it passes through the patient. Accordingly, the user receives visual feedback to help navigate or guide the surgical instrument to the target site.

There are clinical benefits to electromagnetically tracking a portion or entire length of a guidewire that is used in endovascular interventional applications. One benefit is that a user can more efficiently navigate a guidewire to the target site with the aid of a three-dimensional (3D) surgical navigation tracking system. Another benefit is that the tracking system will provide real-time location data of the guidewire to the user, requiring a lower radiation dose from the imaging apparatus.

It is very difficult to incorporate electromagnetically trackable sensors of high signal strength into devices of the sizes provided by typical guidewires having a diameter of less than a 1 mm. These electromagnetically trackable sensors may require a shielded type of electrical connection (e.g., coax or twisted pair) with the surgical navigation tracking system to reduce the introduction of noise into the electromagnetic signal. The sensors must efficiently occupy the volume available to maximize signal strength without affecting the clinical and mechanical performance of the guidewire. The guidewire must be robust for the clinical applications contemplated and the electromagnetically trackable sensors must have minimal impact on the mechanical performance of the guidewire, especially with regards to pushability and steerability.

Therefore, it is desirable to provide a guidewire with rugged integration of a plurality of electromagnetically trackable microsensors into a guidewire with minimal impact on the performance of the guidewire during clinical applications.

BRIEF DESCRIPTION OF THE INVENTION

In an embodiment, a guidewire assembly comprising a proximal end; a distal end with a potted tip; a solid core wire having a tapered distal end and extending between the proximal end and the distal end; a plurality of electromagnetic microsensors spaced-apart on and attached to the solid core wire; and an outer member extending from the potted tip and the proximal end forming an outer covering of the guidewire.

In an embodiment, a guidewire assembly comprising a proximal end; a distal end with a flexible tip; a core wire having a tapered distal end and extending between the proximal end and the flexible tip; a plurality of electromagnetic microsensors spaced-apart within the flexible tip; and an outer member extending from the flexible tip and the proximal end forming an outer covering of the guidewire.

In an embodiment, a guidewire assembly comprising a proximal end; a distal end with a flexible tip; a tubular core extending between the proximal end and the flexible tip; a plurality of electromagnetic microsensors spaced-apart within the flexible tip; and an outer member extending from the flexible tip and the proximal end forming an outer covering of the guidewire.

In an embodiment, a guidewire assembly comprising a proximal end; a distal end with a flexible tip; a tubular core extending between the proximal end and the flexible tip; a plurality of electromagnetic microsensors spaced-apart within the tubular core; and an outer member extending from the flexible tip and the proximal end forming an outer covering of the guidewire.

In an embodiment, a guidewire assembly comprising a proximal end; a flexible distal end with a potted tip; a tubular core extending between the proximal end and the flexible distal end; a plurality of electromagnetic microsensors spaced-apart within the flexible distal end and attached to the tubular core; and an outer covering extending from the flexible distal end and the proximal end.

Various other features, objects, and advantages of the invention will be made apparent to those skilled in the art from the accompanying drawings and detailed description thereof.

BRIEF DESCRIPTION OF THE DRAWINGS

FIG. 6 is a cross-sectional view of the distal end of an exemplary embodiment of a guidewire with a plurality of electromagnetic microsensorors integrated therein;

FIG. 7 is a cross-sectional view of the distal end of an exemplary embodiment of a guidewire with a plurality of electromagnetic microsensorors integrated therein;

FIG. 8 is a cross-sectional view of the distal end of an exemplary embodiment of a guidewire with a plurality of electromagnetic microsensorors integrated therein;

FIG. 9 is a cross-sectional view of an exemplary embodiment of a guidewire with a plurality of electromagnetic microsensorors integrated therein;

FIG. 10 is a perspective view of a portion of an exemplary embodiment of a tubular core member that may be used in the exemplary embodiments of the guidewires of FIGS. 7, 8 and 9;

FIG. 11 is a perspective view of a portion of an exemplary embodiment of a tubular core member that may be used in the exemplary embodiments of the guidewires of FIGS. 7, 8 and 9;

DETAILED DESCRIPTION OF THE INVENTION

Figure 1A:
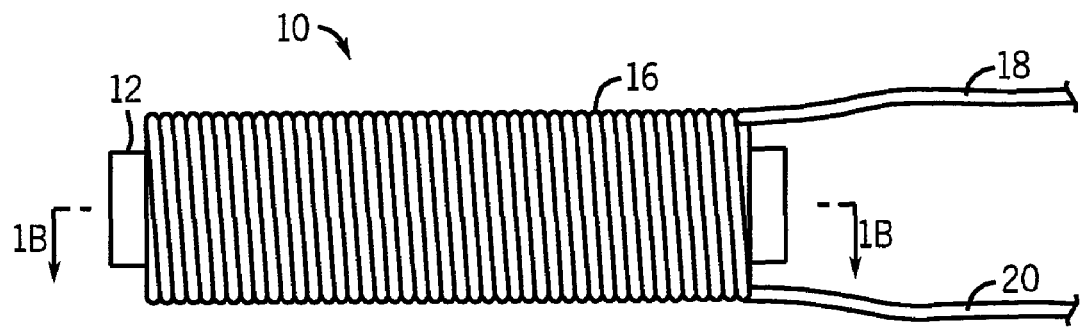
FIG. 1A is a side view of an exemplary embodiment of an electromagnetic microsensor.
Figure 1B:
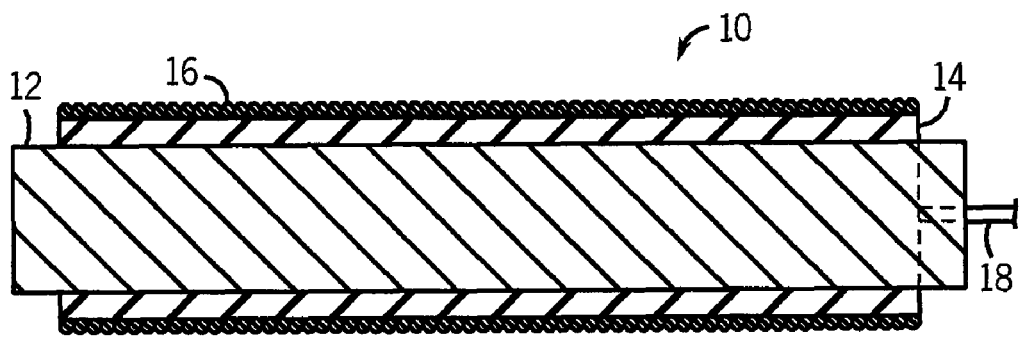
FIG. 1B is a cross-sectional view of the electromagnetic microsensor of FIG. 1A taken along line 1B-1B of FIG. 1A.

Referring to the drawings, FIGS. 1A and 1B illustrate an exemplary embodiment of an electromagnetic microsensor 10. The electromagnetic microsensor 10 is electromagnetically trackable and designed to be integrated into a guidewire for tracking the guidewire during an endovascular procedure with a surgical navigation tracking system. The electromagnetic microsensor 10 includes a hollow or solid core 12 with a plurality of wire windings 16 wound around the hollow or solid core 12. In an exemplary embodiment, a layer of electrical insulation 14 may be included between the hollow or solid core 12 and plurality of wire windings 16. The plurality of wire windings 16 includes a lead wire 18 and a return wire 20 extending therefrom. In an exemplary embodiment, the hollow or solid core 12 may be a solid ferrite rod, a ferrite bead, a ferrite tube, or any solid or a hollow bobbin or mandrel made of any suitable material. In an exemplary embodiment, the microsensor 10 may require a shielded type of electrical connection such as a coaxial cable connection or a twisted pair wire connection with the surgical navigation tracking system to reduce the introduction of noise into the electromagnetic signals. The electrical connection to the electromagnetic microsensor 10 shown in FIGS. 1A and 1B may be a twisted pair electrical connection. A twisted pair electrical connection is a form of wiring in which two conductors are wound together for the purposes of canceling out electromagnetic interference from external sources and crosstalk from neighboring wires. In an exemplary embodiment, the electromagnetic microsensor 10 may be of high signal strength and may be incorporated into guidewires having a diameter of less than a 1 mm.

Figure 2A:
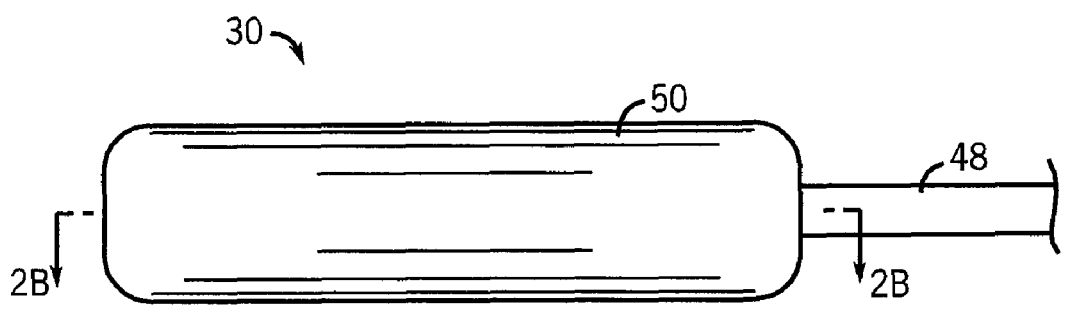
FIG. 2A is a side view of an exemplary embodiment of an electromagnetic microsensor.
Figure 2B:
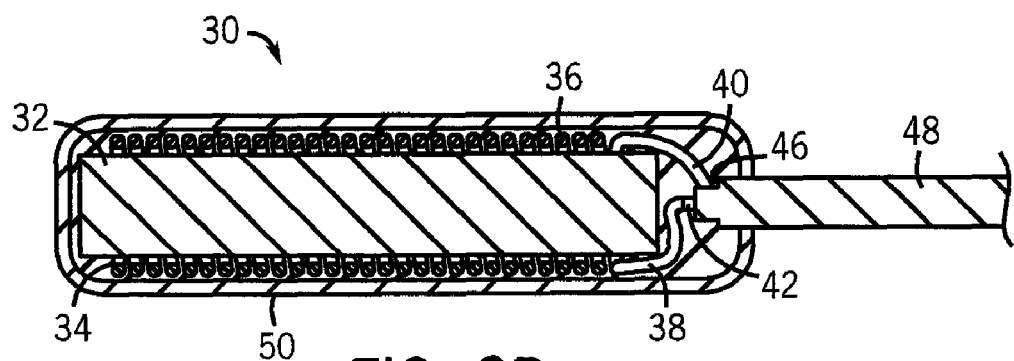
FIG. 2B is a cross-sectional view of the electromagnetic microsensor of FIG. 2A taken along line 2B-2B of FIG. 2A.

FIGS. 2A and 2B illustrate an exemplary embodiment of an electromagnetic microsensor 30. The electromagnetic microsensor 30 is electromagnetically trackable and designed to be integrated into a guidewire for tracking the guidewire during an endovascular procedure with a surgical navigation tracking system. The electromagnetic microsensor 30 includes a hollow or solid core 32 with a plurality of wire windings 36 wound around the hollow or solid core 32. In an exemplary embodiment, a layer of electrical insulation 34 may be included between the hollow or solid core 32 and plurality of wire windings 36. The plurality of wire windings 36 includes a lead wire 38 and a return wire 40 extending therefrom. In an exemplary embodiment, the hollow or solid core 32 may be a solid ferrite rod, a ferrite bead, or a solid or hollow bobbin or mandrel made of any suitable material. In an exemplary embodiment, the microsensor 30 may require a shielded type of electrical connection such as a coaxial cable connection or a twisted pair wire connection with the surgical navigation tracking system to reduce the introduction of noise into the electromagnetic signals. The electrical connection to the electromagnetic microsensor 30 shown in FIGS. 2A and 2B may be a coaxial cable electrical connection. A coaxial cable 48 is a cylindrical cable with a center conductor 42 surrounded by an insulator 44 that, in turn, is surrounded by a tubular shield conductor 46. The lead wire 38 is soldered to the center conductor 42 and the return wire 40 is soldered to the shield conductor 46. In an exemplary embodiment, the electromagnetic microsensor 30 may be encapsulated within an outer member 50 with an encapsulating compound, potting compound, adhesive, epoxy, or resin 52. In an exemplary embodiment, the electromagnetic microsensor 30 may be of high signal strength and may be incorporated into guidewires having a diameter of less than a 1 mm.

Figure 3:
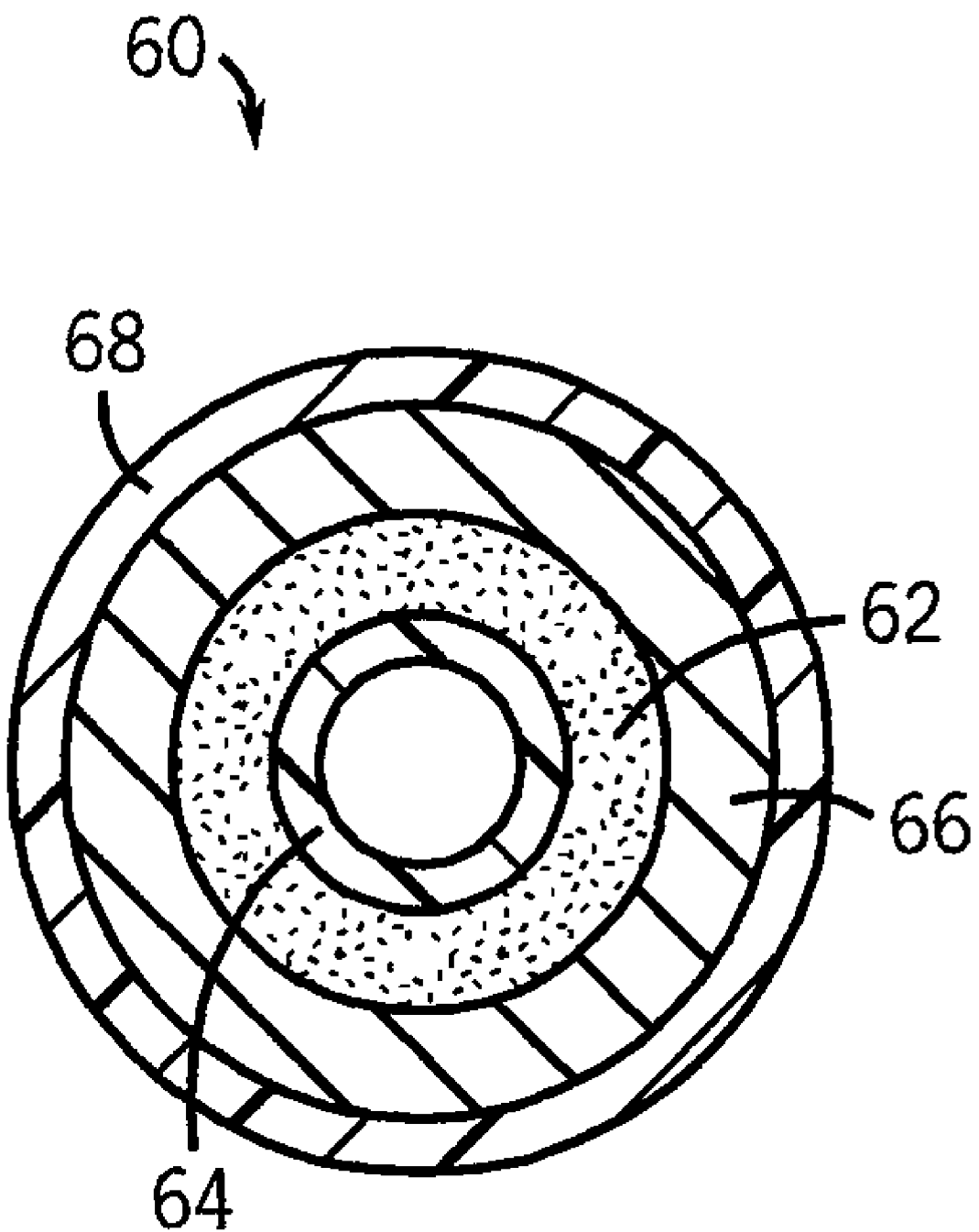
FIG. 3 is a cross-sectional view of an exemplary embodiment of an electromagnetic microsensor.

FIG. 3 illustrates an exemplary embodiment of an electromagnetic microsensor 60 for integration into a guidewire. The electromagnetic microsensor 60 includes a hollow core 62 with a plurality of wire windings 66 wound around the hollow core 62. In an exemplary embodiment, the electromagnetic microsensor 60 includes an inner encapsulation 64 and an outer encapsulation 68 to totally encapsulate the electromagnetic microsensor 60 within an encapsulating compound, potting compound, polymer, epoxy, or resin. In an exemplary embodiment, the hollow core 66 may be a hollow ferrite bead, a hollow ferrite tube, or a hollow bobbin or mandrel made of any suitable material. In an exemplary embodiment, the inner encapsulation 64 and outer encapsulation 68 may be a coating or sleeve of a polymer material. In an exemplary embodiment, the inner encapsulation 64 and hollow core 62 are configured to fit over a core wire of a guidewire.

Figure 4:
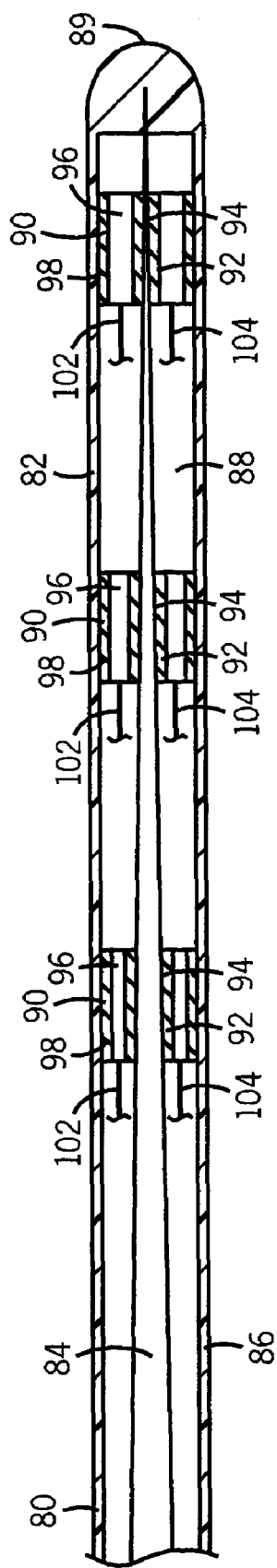
FIG. 4 is a cross-sectional view of the distal end of an exemplary embodiment of a guidewire with a plurality of electromagnetic microsensorors integrated therein.

FIG. 4 illustrates an exemplary embodiment of a guidewire 80 with a plurality of electromagnetic microsensorors 90 integrated therein. The guidewire 80 includes a proximal end (not shown), a distal end 82, a solid core wire 84, a plurality of electromagnetic microsensors 90 spaced-apart from each other and positioned on the core wire 84, an outer member 86 forming an outer covering of the guidewire 80, and a flexible tip 88 at the distal end 82 thereof. The outer member 86 covering the core wire 84 and plurality of electromagnetic microsensors 90. In an exemplary embodiment, the outer member 86 may be an outer sleeve made from a flexible polymer material, a coiled spring or a coiled wire wrapped around the core wire 84 and plurality of electromagnetic microsensors 90. The outer member 86 provides flexibility of the guidewire 80 at the distal end 82 thereof. The flexible tip 88 positioned at the distal end 82 of the guidewire 80 includes a rounded end cap 89. In an exemplary embodiment, the rounded end cap 89 may be made of stainless steel, titanium, a polymer, or any other biocompatible material that can be used within a human or animal body. In an exemplary embodiment, the rounded end cap 89 may be integral with or attached to the outer member 86 of an outer sleeve made from a flexible polymer material with an encapsulating compound, potting compound, adhesive, epoxy, or resin. In an exemplary embodiment, the rounded end cap 89 may be integral with or attached to the outer member 86 of a coiled spring or a coiled wire by welding or soldering the rounded end cap 89 to the end of the outer member 86. The coiled spring or coiled wire may be made of stainless steel, titanium, a polymer, or any other biocompatible material that can be used within a human or animal body.

In an exemplary embodiment, the distal end 82 of the guidewire 80 may be pre-formed to a curved shape where the flexible tip 88 is curved back toward the proximal end forming a J-shape to assist with steering the guidewire 80 through tortuous vessels.

In an exemplary embodiment, the core wire 84 extends from the proximal end to the distal end 82 of the guidewire 80 through the plurality of microsensors 90. The core wire 84 may or may not be tapered toward the distal end 82. The taper may be a gradual taper or a stepped taper toward the distal end 82. The core wire 84 provides stiffness and pushability for the guidewire 80. In an exemplary embodiment, the core wire 84 may be made of a ferromagnetic material to amplify the signal strength of the plurality of microsensors 90.

The plurality of electromagnetic microsensors 90 may include any of the embodiments illustrated in FIG. 1A, 1B, 2A, 2B or 3. Each electromagnetic microsensor 90 includes a hollow core 92 with a plurality of wire windings 96 wound around the hollow core 92. In an exemplary embodiment, each electromagnetic microsensor 90 includes an inner encapsulation 94 and an outer encapsulation 98 to totally encapsulate the electromagnetic microsensor 90 within an encapsulating compound, potting compound, polymer, epoxy, or resin. In an exemplary embodiment, the hollow core 66 may be a hollow ferrite bead, a hollow ferrite tube, or a hollow bobbin or mandrel made of any suitable material. In an exemplary embodiment, the hollow core 92 is configured to fit over the core wire 84 of the guidewire 80. The plurality of microsensors 90 may each have a hollow core 92 with a different diameter to fit over different diameters along a tapered core wire 84. The inner surface of each hollow core 92 is bonded to the outer surface of the core wire 84 with an adhesive, epoxy, or resin. The outer surface of each microsensor 90 is bonded to the inner surface of the outer member 86 with an adhesive, epoxy, or resin.

Each microsensor 90 includes a lead wire 102 and a return wire 104 extending from the plurality of wire windings 96. In an exemplary embodiment, each microsensor 90 may require a shielded type of electrical connection such as a coaxial cable connection or a twisted pair wire connection. In an exemplary embodiment, the lead wires 102 and return wires 104 extending from the plurality of microsensors 90 pass between the core wire 84 and the outer member 86.

Figure 13:
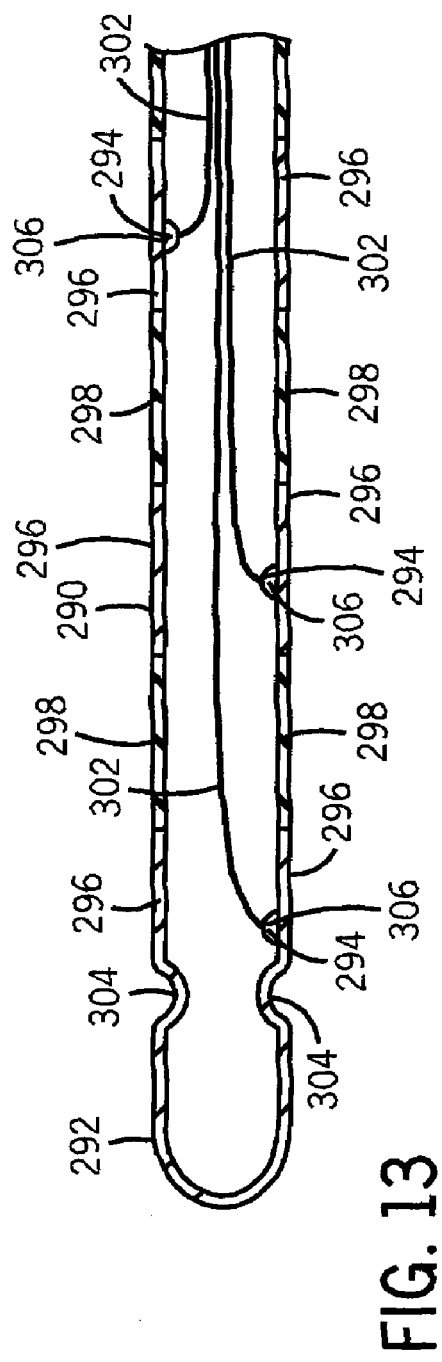
FIG. 13 is a cross-sectional view of the proximal end of an exemplary embodiment of a guidewire with a plurality of electrical connections integrated therein.
Figure 14:
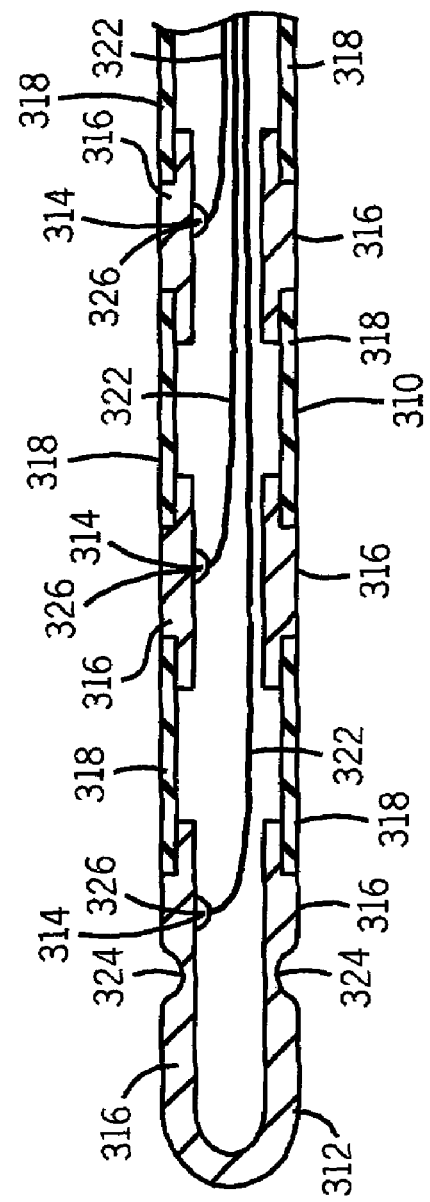
FIG. 14 is a cross-sectional view of the proximal end of an exemplary embodiment of a guidewire with a plurality of electrical connections integrated therein.

The mechanical performance of the guidewire 80 is maintained by spacing a plurality of microsensors 90 along the length of the guidewire's distal end 82 and allowing additional flexibility between each microsensor 90 to compensate for the effective stiffness provided by each microsensor 90 and its wiring. The plurality of microsensors 90 efficiently occupy the volume available in the guidewire 80 to maximize the signal strength of each microsensor 90 without affecting the clinical and mechanical performance of the guidewire 80, especially with regards to pushability and steerability of the guidewire 80. Each exemplary embodiment of guidewire 80 is terminated at its proximal end using in-line connectors 306, 326 as shown in FIGS. 13 and 14, for connecting the lead wires 102 and possibly the return wires 104 from the plurality of microsensors 90 integrated into the guidewires 80 to a surgical navigation system employing electromagnetic tracking technology.

Figure 5:
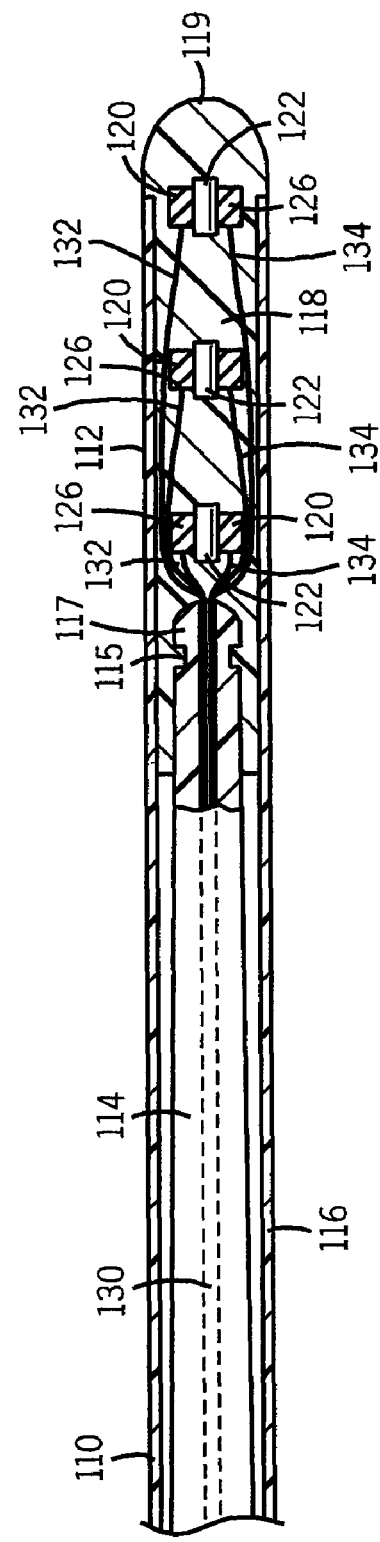
FIG. 5 is a cross-sectional view of the distal end of an exemplary embodiment of a guidewire with a plurality of electromagnetic microsensorors integrated therein.

FIG. 5 illustrates an exemplary embodiment of a guidewire 110 with a plurality of electromagnetic microsensorors 120 integrated therein. The guidewire 110 includes a proximal end (not shown), a distal end 112, a core wire 114, a molded flexible tip 118, a plurality of electromagnetic microsensors 120 spaced-apart from each other and embedded within the molded flexible tip 118, and an outer member 116 forming an outer covering of the guidewire 110. The outer member 116 covering the core wire 114, molded flexible tip 118, and plurality of electromagnetic microsensors 120. In an exemplary embodiment, the outer member 116 may be an outer sleeve made from a flexible polymer material, a coiled spring or a coiled wire wrapped around the core wire 114 and plurality of electromagnetic microsensors 120. The outer member 116 extends around the molded flexible tip 118. The outer member 116 and molded flexible tip 118 provide flexibility of the guidewire 110 at the distal end 112 thereof. The molded flexible tip 118 positioned at the distal end 112 of the guidewire 110 includes a rounded end cap 119. In an exemplary embodiment, the molded flexible tip 118 may be made from an encapsulating compound, potting compound, polymer, epoxy, or resin with the plurality of microsensors 120 embedded therein. In an exemplary embodiment, the rounded end cap 119 may be made of stainless steel, titanium, a polymer, or any other biocompatible material that can be used within a human or animal body. In an exemplary embodiment, the rounded end cap 119 may be integral with or attached to the outer member 116 of an outer sleeve made from a flexible polymer material with an encapsulating compound, potting compound, adhesive, epoxy, or resin. In an exemplary embodiment, the rounded end cap 119 may be integral with or attached to the outer member 116 of a coiled spring or a coiled wire by welding or soldering the rounded end cap 119 to the end of the outer member 116. The coiled spring or coiled wire may be made of stainless steel, titanium, a polymer, or any other biocompatible material that can be used within a human or animal body.

In an exemplary embodiment, the distal end 112 of the guidewire 110 may be pre-formed to a curved shape where the molded flexible tip 118 is curved back toward the proximal end forming a J-shape to assist with steering the guidewire 110 through tortuous vessels.

In an exemplary embodiment, the core wire 114 is a solid core wire that is tapered toward the distal end 117 thereof and extends into the molded flexible tip 118. The taper may be a gradual taper or a stepped taper toward the distal end 117. The distal end 117 of the core wire 114 includes a keying feature 115 to better retain the molded flexible tip 118 on the core wire 114 and the guidewire 110. The core wire 114 provides stiffness and pushability for the guidewire 110.

The plurality of electromagnetic microsensors 120 may include any of the embodiments illustrated in FIG. 1A, 1B, 2A, 2B or 3. The plurality of microsensors 120 are embedded within the molded flexible tip 118. Each electromagnetic microsensor 120 includes a solid or hollow core 122 with a plurality of wire windings 126 wound around the core 122. In an exemplary embodiment, the core 122 may be a solid ferrite core, hollow ferrite bead, a hollow ferrite tube, or a solid or hollow bobbin or mandrel made of any suitable material.

Each microsensor 120 includes a lead wire 132 and a return wire 134 extending from the plurality of wire windings 126. In an exemplary embodiment, each microsensor 120 may require a shielded type of electrical connection such as a coaxial cable connection or a twisted pair wire connection. In an exemplary embodiment, the lead wires 132 and return wires 134 extending from the plurality of microsensors 120 pass between the core wire 114 and the outer member 116.

In an exemplary embodiment, the core wire 114 is a hollow core wire with an opening 130 extending therethrough, and is tapered toward the distal end 117 thereof and extends into the molded flexible tip 118. In an exemplary embodiment, the distal end 117 may include a keying feature 115 to better retain the molded flexible tip 118 on the core wire 114 and the guidewire 110. The core wire 114 provides stiffness and pushability for the guidewire 110. The lead wires 132 and return wires 134 extending from the plurality of microsensors 120 pass through the opening 130 within the core wire 114.

The mechanical performance of the guidewire 110 is maintained by spacing a plurality of microsensors 120 along the length of the guidewire's molded flexible tip 118 and allowing additional flexibility between each microsensor 120 to compensate for the effective stiffness provided by each microsensor 120 and its wiring. The plurality of microsensors 120 efficiently occupy the volume available in the molded flexible tip 118 to maximize the signal strength of each microsensor 120 without affecting the clinical and mechanical performance of the guidewire 110, especially with regards to pushability and steerability of the guidewire 110. Each exemplary embodiment of guidewire 110 is terminated at its proximal end using in-line connectors 306, 326 as shown in FIGS. 13 and 14, for connecting the lead wires 132 and possibly the return wires 134 from the plurality of microsensors 120 integrated into the guidewires 110 to a surgical navigation system employing electromagnetic tracking technology.

FIG. 6 illustrates an exemplary embodiment of a guidewire 140 with a plurality of electromagnetic microsensorors 150 integrated therein. The guidewire 140 includes a proximal end (not shown), a distal end 142, a core wire 144, a flexible tip 148, a plurality of electromagnetic microsensors 150 spaced-apart from each other and mounted within the flexible tip 148, and an outer member 146 forming an outer covering of the guidewire 140. The outer member 146 covering the core wire 144 and portions of the flexible tip 148. In an exemplary embodiment, the outer member 146 may be an outer sleeve made from a flexible polymer material, a coiled spring or a coiled wire wrapped around the core wire 144 and portions of the flexible tip 148. The outer member 146 and flexible tip 148 provide flexibility of the guidewire 140 at the distal end 142 thereof. The outer member 146 and flexible tip 148 provides flexibility of the guidewire 140 at the distal end 142 thereof. In an exemplary embodiment, the flexible tip 148 includes a plurality of tubular members 166 spaced-apart from each other and spaced between sections of outer member 146 within the flexible tip 148. The plurality of tubular members 166 are bonded to the sections of outer member 146 with an adhesive, epoxy, or resin. In an exemplary embodiment, the plurality of microsensors 150 are mounted within the plurality of tubular members 166 within the flexible tip 148. The outer surface of each microsensor 150 is bonded to the inner surface of each tubular member 166 with an adhesive, epoxy, or resin. This exemplary embodiment allows each microsensor 150 to occupy the maximum volume and, consequently, output the highest signal strength. In an exemplary embodiment, the plurality of tubular members 166 may be made of stainless steel, titanium, a polymer, or any other biocompatible material that can be used within a human or animal body. In an exemplary embodiment, the plurality of tubular members 166 may be integral with or attached to sections of outer member 146 of an outer sleeve made from a flexible polymer material with an encapsulating compound, potting compound, adhesive, epoxy, or resin. In an exemplary embodiment, the plurality of tubular members 166 may be integral with or attached to sections of outer member 146 of a coiled spring or a coiled wire by welding or soldering the plurality of tubular members 166 to sections of outer member 146. The coiled spring or coiled wire may be made of stainless steel, titanium, a polymer, or any other biocompatible material that can be used within a human or animal body. The flexible tip 148 positioned at the distal end 142 of the guidewire 140 having a rounded end cap 149. In an exemplary embodiment, the rounded end cap 149 may be made of stainless steel, titanium, a polymer, or any other biocompatible material that can be used within a human or animal body. In an exemplary embodiment, the rounded end cap 149 may be integral with or attached to the outer member 146 of an outer sleeve made from a flexible polymer material with an encapsulating compound, potting compound, adhesive, epoxy, or resin. In an exemplary embodiment, the rounded end cap 149 may be integral with or attached to the outer member 146 of a coiled spring or a coiled wire by welding or soldering the rounded end cap 149 to the end of the outer member 146. The coiled spring or coiled wire may be made of stainless steel, titanium, a polymer, or any other biocompatible material that can be used within a human or animal body.

In an exemplary embodiment, the distal end 142 of the guidewire 140 may be pre-formed to a curved shape where the flexible tip 148 is curved back toward the proximal end forming a J-shape to assist with steering the guidewire 140 through tortuous vessels.

In an exemplary embodiment, the core wire 144 is a solid core wire that is tapered toward the distal end 147 thereof and extends into the flexible tip 148. The taper may be a gradual taper or a stepped taper toward the distal end 147. The core wire 144 provides stiffness and pushability for the guidewire 140.

The plurality of electromagnetic microsensors 150 may include any of the embodiments illustrated in FIG. 1A, 1B, 2A, 2B or 3. In an exemplary embodiment, the plurality of microsensors 150 are mounted within the plurality of tubular members 166 within the flexible tip 148. The outer surface of each microsensor 150 is bonded to the inner surface of each tubular member 166 with an adhesive, epoxy, or resin. Each electromagnetic microsensor 150 includes a solid or hollow core 152 with a plurality of wire windings 156 wound around the core 152. In an exemplary embodiment, the core 152 may be a solid ferrite core, hollow ferrite bead, a hollow ferrite tube, or a solid or hollow bobbin or mandrel made of any suitable material.

Each microsensor 150 includes a lead wire 162 and a return wire 164 extending from the plurality of wire windings 156. In an exemplary embodiment, each microsensor 150 may require a shielded type of electrical connection such as a coaxial cable connection or a twisted pair wire connection. In an exemplary embodiment, the lead wires 162 and return wires 164 extending from the plurality of microsensors 150 pass between the core wire 144 and the outer member 146.

In an exemplary embodiment, the core wire 144 is a hollow core wire with an opening (not shown) extending therethrough, and is tapered toward the distal end 147 thereof and extends into the flexible tip 148. The core wire 144 provides stiffness and pushability for the guidewire 140. The lead wires 162 and return wires 164 extending from the plurality of microsensors 150 pass through the opening within the core wire 144.

The mechanical performance of the guidewire 140 is maintained by spacing a plurality of microsensors 150 along the length of the guidewire's distal end 142 and allowing additional flexibility between each microsensor 150 to compensate for the effective stiffness provided by each microsensor 150 and its wiring. The plurality of microsensors 150 efficiently occupy the volume available in the guidewire 140 to maximize the signal strength of each microsensor 150 without affecting the clinical and mechanical performance of the guidewire 140, especially with regards to pushability and steerability of the guidewire 140. Each exemplary embodiment of guidewire 140 is terminated at its proximal end using in-line connectors 306, 326 as shown in FIGS. 13 and 14, for connecting the lead wires 162 and possibly the return wires 164 from the plurality of microsensors 150 integrated into the guidewires 140 to a surgical navigation system employing electromagnetic tracking technology.

FIG. 7 illustrates an exemplary embodiment of a guidewire 170 with a plurality of electromagnetic microsensorors 180 integrated therein. The guidewire 170 includes a proximal end (not shown), a distal end 172, a tubular core member 174, a flexible tip 178, a plurality of electromagnetic microsensors 180 spaced-apart from each other and embedded within the flexible tip 178, and an outer member 176 forming an outer covering of the guidewire 170. The outer member 176 covers the tubular core member 174, flexible tip 178, and plurality of electromagnetic microsensors 180. In an exemplary embodiment, the outer member 176 may be an outer sleeve made from a flexible polymer material, a coiled spring or a coiled wire wrapped around the tubular core member 174 and plurality of electromagnetic microsensors 180. The outer member 176 extends around the flexible tip 178. The outer member 176 and flexible tip 178 provide flexibility of the guidewire 170 at the distal end 172 thereof. The flexible tip 178 positioned at the distal end 172 of the guidewire 170 includes a rounded end cap 179. In an exemplary embodiment, the flexible tip 178 may be made from an encapsulating compound, potting compound, polymer, epoxy, or resin with the plurality of microsensors 180 embedded therein. In an exemplary embodiment, the rounded end cap 179 may be made of stainless steel, titanium, a polymer, or any other biocompatible material that can be used within a human or animal body. In an exemplary embodiment, the rounded end cap 179 may be integral with or attached to the outer member 176 of an outer sleeve made from a flexible polymer material with an encapsulating compound, potting compound, adhesive, epoxy, or resin. In an exemplary embodiment, the rounded end cap 179 may be integral with or attached to the outer member 176 of a coiled spring or a coiled wire by welding or soldering the rounded end cap 179 to the end of the outer member 176. The coiled spring or coiled wire may be made of stainless steel, titanium, a polymer, or any other biocompatible material that can be used within a human or animal body. In an exemplary embodiment, the tubular core member 174 is hollow with an opening 196 extending therethrough. The tubular core member 174 extends into the flexible tip 178. The tubular core member 174 may be made of Nitinol, stainless steel, titanium, a polymer, or any other biocompatible material that can be used within a human or animal body with varying stiffness. The tubular core member 174 may include grooves 198 extending therethrough that improve flexibility as shown in FIGS. 10 and 11. The tubular core member 174 provides stiffness and pushability for the guidewire 170.

In an exemplary embodiment, the distal end 172 of the guidewire 170 may be pre-formed to a curved shape where the flexible tip 178 is curved back toward the proximal end forming a J-shape to assist with steering the guidewire 170 through tortuous vessels.

The plurality of electromagnetic microsensors 180 may include any of the embodiments illustrated in FIG. 1A, 1B, 2A, 2B or 3. The plurality of microsensors 180 are embedded within the flexible tip 178. Each electromagnetic microsensor 180 includes a solid or hollow core 182 with a plurality of wire windings 186 wound around the core 182. In an exemplary embodiment, the core 182 may be a solid ferrite core, hollow ferrite bead, or hollow mandrel to maximize signal strength. In an exemplary embodiment, the core 182 may be a solid ferrite core, hollow ferrite bead, a hollow ferrite tube, or a solid or hollow bobbin or mandrel made of any suitable material.

Each microsensor 180 includes a lead wire 192 and a return wire (not shown) extending from the plurality of wire windings 186. The lead wires 192 and return wires extend from the plurality of microsensors 180. In an exemplary embodiment, each microsensor 180 may require a shielded type of electrical connection such as a coaxial cable connection or a twisted pair wire connection. In an exemplary embodiment, the lead wires 192 and return wires extending from the plurality of microsensors 180 pass through the opening 196 in the tubular core member 174. In an exemplary embodiment, the return wire from each microsensor 180 may be electrically connected to the tubular core member 174 to create an effective coaxial type connection with a shared return shield. The tubular core member 174 may be electrically insulated from the outer member 176 by an insulating layer.

The mechanical performance of the guidewire 170 is maintained by spacing a plurality of microsensors 180 along the length of the guidewire's flexible tip 178 and allowing additional flexibility between each microsensor 180 to compensate for the effective stiffness provided by each microsensor 180 to compensate for the effective stiffness provided by each microsensor 120 and its wiring. The plurality of microsensors 180 efficiently occupy the volume available in the flexible tip 178 to maximize the signal strength of each microsensor 180 without affecting the clinical and mechanical performance of the guidewire 170, especially with regards to pushability and steerability of the guidewire 170. Each exemplary embodiment of guidewire 170 is terminated at its proximal end using in-line connectors 306, 326 as shown in FIGS. 13 and 14, for connecting the lead wires 192 and possibly the return wires from the plurality of microsensors 180 integrated into the guidewires 170 to a surgical navigation system employing electromagnetic tracking technology.

FIG. 8 illustrates an exemplary embodiment of a guidewire 210 with a plurality of electromagnetic microsensorors 220 integrated therein. The guidewire 210 includes a proximal end (not shown), a distal end 212, a tubular core member 214, a flexible tip 218, a plurality of electromagnetic microsensors 220 spaced-apart from each other and mounted within the flexible tip 218, and an outer member 216 forming an outer covering of the guidewire 210. The outer member 216 covers the tubular core member 214, flexible tip 218, and plurality of electromagnetic microsensors 220. In an exemplary embodiment, the outer member 216 may be an outer sleeve made from a flexible polymer material, a coiled spring or a coiled wire wrapped around the tubular core member 214 and plurality of electromagnetic microsensors 220. The outer member 216 and flexible tip 218 provide flexibility of the guidewire 210 at the distal end 212 thereof. The flexible tip 218 positioned at the distal end 212 of the guidewire 210 includes a rounded end cap 219. In an exemplary embodiment, the rounded end cap 219 may be made of stainless steel, titanium, a polymer, or any other biocompatible material that can be used within a human or animal body. In an exemplary embodiment, the rounded end cap 219 may be integral with or attached to the outer member 216 of an outer sleeve made from a flexible polymer material with an encapsulating compound, potting compound, adhesive, epoxy, or resin. In an exemplary embodiment, the rounded end cap 219 may be integral with or attached to the outer member 216 of a coiled spring or a coiled wire by welding or soldering the rounded end cap 219 to the end of the outer member 216. The coiled spring or coiled wire may be made of stainless steel, titanium, a polymer, or any other biocompatible material that can be used within a human or animal body. In an exemplary embodiment, the tubular core member 214 is hollow with an opening 236 extending therethrough. The tubular core member 214 extends through the guidewire 210 to the rounded end cap 219. The tubular core member 214 may be made of Nitinol, stainless steel, titanium, a polymer, or any other biocompatible material that can be used within a human or animal body with varying stiffness. The tubular core member 214 may include grooves 238 extending therethrough that improve flexibility as shown in FIGS. 10 and 11. The tubular core member 214 provides stiffness and pushability for the guidewire 210.

In an exemplary embodiment, the distal end 212 of the guidewire 210 may be pre-formed to a curved shape where the flexible tip 218 is curved back toward the proximal end forming a J-shape to assist with steering the guidewire 210 through tortuous vessels.

The plurality of electromagnetic microsensors 220 may include any of the embodiments illustrated in FIG. 1A, 1B, 2A, 2B or 3. The plurality of microsensors 220 are mounted to the tubular core member 214 within the flexible tip 218. The outer surface of each microsensor 220 is bonded to the inner surface of the tubular core member 214 with an adhesive, epoxy, or resin. Each electromagnetic microsensor 220 includes a solid or hollow core 222 with a plurality of wire windings 226 wound around the core 222. In an exemplary embodiment, the core 222 may be a solid ferrite core, hollow ferrite bead, or hollow mandrel to maximize signal strength. In an exemplary embodiment, the core 222 may be a solid ferrite core, hollow ferrite bead, a hollow ferrite tube, or a solid or hollow bobbin or mandrel made of any suitable material.

Each microsensor 220 includes a lead wire 232 and a return wire (not shown) extending from the plurality of wire windings 226. The lead wires 232 and return wires extend from the plurality of microsensors 220. In an exemplary embodiment, each microsensor 220 may require a shielded type of electrical connection such as a coaxial cable connection or a twisted pair wire connection. In an exemplary embodiment, the lead wires 232 and return wires extending from the plurality of microsensors 220 pass through the opening 236 in the tubular core member 214. In an exemplary embodiment, the return wire from each microsensor 220 is electrically connected to the tubular core member 214 to create an effective coaxial type connection with a shared return shield. The tubular core member 214 may be electrically insulated from the outer member 216 by an insulating layer.

The mechanical performance of the guidewire 210 is maintained by spacing a plurality of microsensors 220 along the length of the guidewire's flexible tip 218 and allowing additional flexibility between each microsensor 220 to compensate for the effective stiffness provided by each microsensor 220 to compensate for the effective stiffness provided by each microsensor 220 and its wiring. The plurality of microsensors 220 efficiently occupy the volume available in the flexible tip 218 to maximize the signal strength of each microsensor 220 without affecting the clinical and mechanical performance of the guidewire 210, especially with regards to pushability and steerability of the guidewire 210. Each exemplary embodiment of guidewire 210 is terminated at its proximal end using in-line connectors 306, 326 as shown in FIGS. 13 and 14, for connecting the lead wires 232 and possibly the return wires from the plurality of microsensors 220 integrated into the guidewires 210 to a surgical navigation system employing electromagnetic tracking technology.

FIG. 9 illustrates an exemplary embodiment of a guidewire 240 with a plurality of electromagnetic microsensors 250 integrated therein. The guidewire 240 includes a proximal end (not shown), a distal end 242, a tubular core member 244, a plurality of electromagnetic microsensors 250 spaced-apart from each other and mounted within a distal end 247 of the tubular core member 244, an insulating layer member 245 surrounding the tubular core member 244, an outer member 246 surrounding the insulating layer member 245 and forming an outer covering of the guidewire 240, and a flexible tip 248 at the distal end 242 thereof. The outer member 246 covers the tubular core member 244, insulating layer member 245, and plurality of electromagnetic microsensors 250 at the flexible tip 248. In an exemplary embodiment, the outer member 216 may be an outer sleeve made from a flexible polymer material, a coiled spring or a coiled wire wrapped around the insulating layer member 245 and the tubular core member 244 and plurality of electromagnetic microsensors 250. The outer member 246 and flexible tip 248 provide flexibility of the guidewire 240 at the distal end 242 thereof. The flexible tip 248 positioned at the distal end 242 of the guidewire 240 includes a rounded end cap 249. In an exemplary embodiment, the rounded end cap 249 may be made of stainless steel, titanium, a polymer, or any other biocompatible material that can be used within a human or animal body. In an exemplary embodiment, the rounded end cap 249 may be integral with or attached to the insulating layer member 245 and/or outer member 246 of an outer sleeve made from a flexible polymer material with an encapsulating compound, potting compound, adhesive, epoxy, or resin. In an exemplary embodiment, the rounded end cap 249 may be integral with or attached to the outer member 246 of a coiled spring or a coiled wire by welding or soldering the rounded end cap 249 to the end of the outer member 246. The coiled spring or coiled wire may be made of stainless steel, titanium, a polymer, or any other biocompatible material that can be used within a human or animal body. In an exemplary embodiment, the tubular core member 244 is hollow with an opening 266 extending therethrough. The tubular core member 244 extends through the guidewire 240 to the rounded end cap 249. The tubular core member 244 may be made of Nitinol, stainless steel, titanium, a polymer, or any other biocompatible material that can be used within a human or animal body with varying stiffness. The tubular core member 244 may include grooves 268 extending therethrough that improve flexibility as shown in FIGS. 10 and 11. The tubular core member 244 provides stiffness and pushability for the guidewire 240.

In an exemplary embodiment, the distal end 242 of the guidewire 240 may be pre-formed to a curved shape where the flexible tip 248 is curved back toward the proximal end forming a J-shape to assist with steering the guidewire 240 through tortuous vessels.

The plurality of electromagnetic microsensors 250 may include any of the embodiments illustrated in FIG. 1A, 1B, 2A, 2B or 3. The plurality of microsensors 250 are mounted to the tubular core member 244. The outer surface of each microsensor 250 is bonded to the inner surface of the tubular core member 244 with an adhesive, epoxy, or resin. Each electromagnetic microsensor 250 includes a solid or hollow core 252 with a plurality of wire windings 256 wound around the core 252. In an exemplary embodiment, the core 252 may be a solid ferrite core, hollow ferrite bead, or hollow mandrel to maximize signal strength. In an exemplary embodiment, the core 252 may be a solid ferrite core, hollow ferrite bead, a hollow ferrite tube, or a solid or hollow bobbin or mandrel made of any suitable material.

Each microsensor 250 includes a lead wire 262 and a return wire 264 extending from the plurality of wire windings 256. The lead wires 262 and return wires 264 extend from the plurality of microsensors 250. In an exemplary embodiment, each microsensor 250 may require a shielded type of electrical connection such as a coaxial cable connection or a twisted pair wire connection. In an exemplary embodiment, the lead wires 262 and return wires extending from the plurality of microsensors 250 pass through the opening 266 in the tubular core member 244. In an exemplary embodiment, the return wire 264 from each microsensor 250 is electrically connected to the tubular core member 244 to create an effective coaxial type connection with a shared return shield. The tubular core member 244 is electrically insulated from the outer member 246 by an insulating layer 245.

The mechanical performance of the guidewire 240 is maintained by spacing a plurality of microsensors 250 along the length of the guidewire's flexible tip 248 and allowing additional flexibility between each microsensor 250 to compensate for the effective stiffness provided by each microsensor 250 to compensate for the effective stiffness provided by each microsensor 250 and its wiring. The plurality of microsensors 250 efficiently occupy the volume available in the flexible tip 248 to maximize the signal strength of each microsensor 250 without affecting the clinical and mechanical performance of the guidewire 240, especially with regards to pushability and steerability of the guidewire 240. Each exemplary embodiment of guidewire 240 is terminated at its proximal end using in-line connectors 306, 326 as shown in FIGS. 13 and 14, for connecting the lead wires 262 and possibly the return wires from the plurality of microsensors 250 integrated into the guidewires 240 to a surgical navigation system employing electromagnetic tracking technology.

FIG. 10 is a perspective view of a portion of an exemplary embodiment of a tubular core member 174, 214, 244 of the guidewires 170, 210, 240 of FIGS. 7, 8 and 9. The tubular core member 174, 214, 244 includes a helical spiral of grooves 198, 238, 268 formed in the tubular core member 174, 214, 244. In FIGS. 8 and 9, the microsensors 180, 220, 250 are spaced-apart along the length of the tubular core member 174, 214, 244 and located between the grooves 198, 238, 268 allowing additional flexibility between each microsensor 180, 220, 250 to compensate for the effective stiffness provided by each microsensor 180, 220, 250 and its wiring. The grooves 198, 238, 268 can be located at the distal end or along the entire length of the guidewire. The pitch and thickness of the grooves 198, 238, 268 can be adjusted to vary the stiffness of the guidewire.

FIG. 11 is a perspective view of a portion of an exemplary embodiment of a tubular member 174, 214, 244 of the guidewires 170, 210, 240 of FIGS. 7, 8 and 9. The tube member 174, 214, 244 includes grooves 198, 238, 268 formed in the tubular core member 174, 214, 244. The grooves 198, 238, 268 allowing additional flexibility. The grooves 198, 238, 268 can be located at the distal end or along the entire length of the guidewire. The pitch, thickness, and length of the grooves 198, 238, 268 can be adjusted to vary the stiffness of the guidewire.

In an exemplary embodiment, a plurality of microsensors are embedded in a polymer in a flexible tip of a guidewire. The method of embedding the microsensors may be by low-pressure injection molding, dip molding, potting, or any other suitable method. In an exemplary embodiment, a plurality of microsensors are bonded to the inner surface of a tubular core member. In these exemplary embodiments, the microsensor lead wires are passed through an opening in the tubular core member. The tubular core member itself may be used as a return for the plurality of microsensors as described in FIG. 12 below. Both exemplary embodiments may have varying stiffness by having grooves or cuts formed within the tubular core member.

Figure 12:
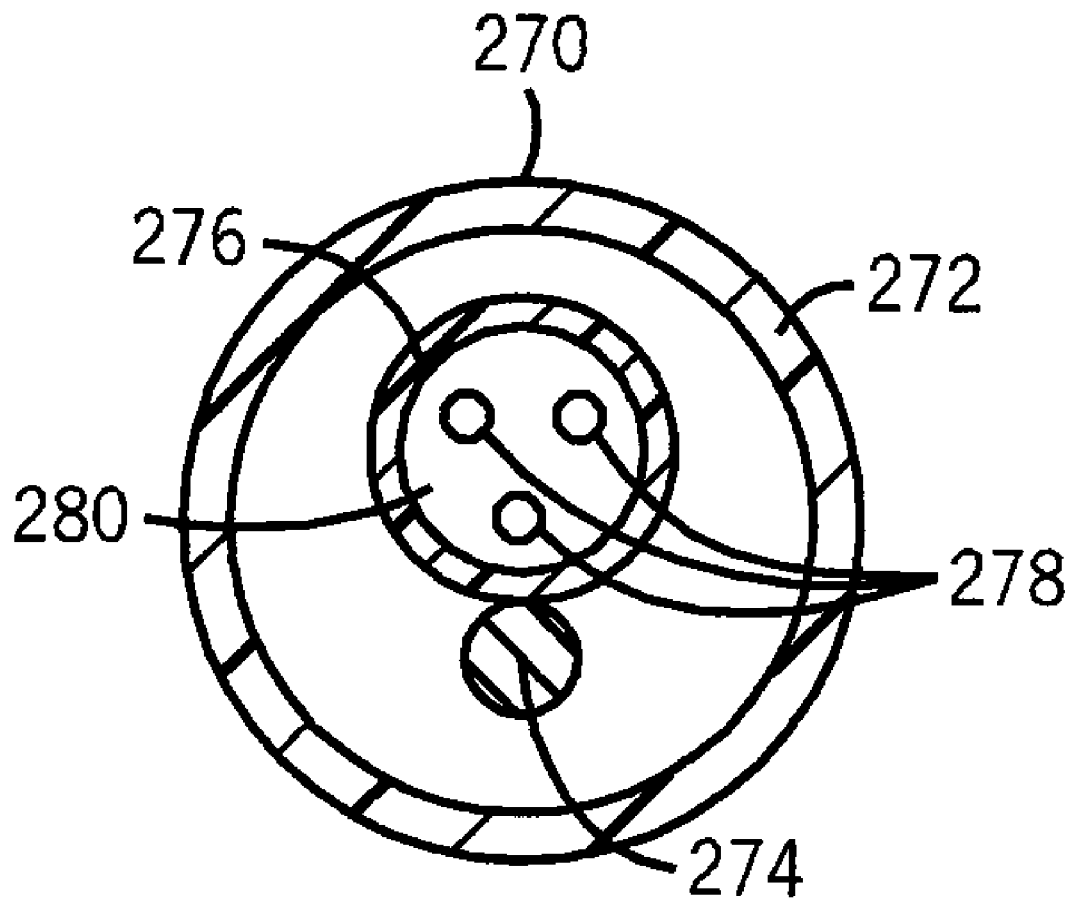
FIG. 12 is a cross-sectional view of an exemplary embodiment of a guidewire illustrating a common return and lead wires from a plurality of electromagnetic microsensors extending through the guidewire.

FIG. 12 illustrates an exemplary embodiment of a guidewire 270 illustrating a common return for a plurality of return wires from a plurality of microsensors integrated within the guidewire and a plurality of lead wires from the plurality of electromagnetic microsensors that extend through the guidewire. The guidewire 270 includes an outer member 272, a core wire or tubular core member 274, and a cable connection 276 with a plurality of inner conductors 278 for connection to a plurality or lead wires from a plurality of microsensors and a common return shield 280 for connection to a plurality of return wires from the plurality of microsensors integrated within the guidewire. This exemplary embodiment illustrates a connection method for optimizing volume in the guidewire by using a technique that minimizes the number of conductors needed to power individual microsensors. Each microsensor requires a positive current lead and a return lead. However, multiple microsensors can share the same return lead. The return lead can be connected to an outer shield to reduce signal noise. By reducing the number of leads for a given number of microsensors, the manufacturing process can be simplified and more volume is available for maximizing the number of microsensors that can be integrated into a guidewire.

FIGS. 13 and 14 illustrate exemplary embodiments of proximal in-line connectors 306, 326 for connecting lead wires from a plurality of microsensors integrated into a guidewire to a surgical navigation system employing electromagnetic tracking technology. To optimize the available volume in each exemplary embodiment for electrical connections between the plurality of microsensors and the proximal in-line connectors, each exemplary embodiment may utilize the method illustrated in FIG. 12.

FIG. 13 illustrates the proximal end 292 of an exemplary embodiment of a guidewire 290 with a plurality of electrical connections 294 integrated therein. The proximal end 292 of the guidewire 290 includes alternating conductor members 296 and insulating members 298 forming an outer surface of the proximal end 292 of the guidewire 290. The alternating conductor members 296 and insulating members 298 may be bonded together with an adhesive, epoxy, or resin. A plurality of microsensor lead wires 302 are soldered to the conductor members 296 at the electrical connections 294 for connection to a surgical navigation tracking system. The plurality of electrical connections 294 and the conductor members 296 forming in-line connectors 306 for the guidewire 290. The proximal end 292 of the guidewire 290 further includes at least one locking member 304 formed in the proximal end 292 thereof for mating with a receptacle of a guidewire/catheter system.

FIG. 14 illustrates the proximal end 312 of an exemplary embodiment of a guidewire 310 with a plurality of electrical connections 314 integrated therein. The proximal end 312 of the guidewire 310 includes alternating conductor members 316 and insulating members 318 forming an outer surface of the proximal end 312 of the guidewire 310. The alternating conductor members 316 and insulating members 318 may be bonded together with an adhesive, epoxy, or resin. A plurality of microsensor lead wires 322 are soldered to the conductor members 316 at the electrical connections 314 for connection to a surgical navigation tracking system. The plurality of electrical connections 314 and the conductor members 316 forming in-line connectors 326 for the guidewire 310. The proximal end 312 of the guidewire 310 further includes at least one locking member 324 formed in the proximal end 312 thereof for mating with a receptacle of a guidewire/catheter system.

It should be appreciated that according to alternate exemplary embodiments, the electromagnetic microsensor may be an electromagnetic sensor, an electromagnetic receiver, an electromagnetic field generator (transmitter), or any combination thereof.

The exemplary embodiments described herein provide specific, feasible apparatus, systems, and methods of integrating electromagnetically trackable microsensors into guidewires that do not currently exist. By integrating microsensors into guidewires in a robust and clinically effective way, minimally invasive surgical techniques and interventional procedures, can utilize electromagnetic tracking technology to provide more efficient treatments, less radiation dose, and faster procedures.

The exemplary embodiments of guidewires described herein may be used as part of a surgical navigation system employing electromagnetic tracking technology that may be used in an interventional suite. The surgical navigation system may be integrated into a fixed C-arm system, a portable C-arm system, or a stand-alone tracking system.

Several embodiments are described above with reference to drawings. These drawings illustrate certain details of specific embodiments that implement the apparatus, systems, and methods of the disclosure. However, the drawings should not be construed as imposing any limitations associated with features shown in the drawings.

The foregoing description of exemplary embodiments has been presented for purposes of illustration and description. It is not intended to be exhaustive or to limit the invention to the precise form disclosed, and modifications and variations are possible in light of the above teachings or may be acquired from practice of the disclosure. The embodiments were chosen and described in order to explain the principles of the invention and its practical application to enable one skilled in the art to utilize the invention in various embodiments and with various modifications as are suited to the particular use contemplated.

While the disclosure has been described with reference to exemplary embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A guidewire assembly comprising:
  a guidewire having:
    a proximal end;
    a distal end;
    a solid core wire extending between the proximal end and the distal end;
    a plurality of electromagnetic microsensors having a hollow ferrite core, wherein the plurality of electromagnetic microsensors are spaced apart from each other and positioned on the solid core wire so that the solid core wire extends through the hollow ferrite core of the plurality of electromagnetic microsensors;
    an outer member forming an outer covering of the guidewire; and
    a flexible tip positioned at the distal end of the guidewire.

2. The guidewire of claim 1, wherein the outer member comprises an outer sleeve comprising a flexible polymer material, a coiled spring, or a coiled wire wrapped around the solid core wire and the plurality of electromagnetic microsensors.

3. The guidewire of claim 1, wherein the solid core wire tapers towards the guidewire's distal end and wherein the hollow ferrite core of each of the plurality of electromagnetic microsensors comprises a different diameter to fit over the tapered solid core wire.

4. The guidewire of claim 1, wherein an inner surface of the hollow ferrite core is bonded to an outer surface of the solid core wire with a bond material.

5. The guidewire of claim 1, wherein each electromagnetic microsensor is bonded to an inner surface of the outer member with a bond material.

6. The guidewire of claim 1, wherein each electromagnetic microsensor includes a lead wire and a return wire extending from the plurality of wire windings wound around the hollow ferrite core.

7. The guidewire of claim 6, wherein each return wire from the plurality of electromagnetic microsensors is connected to a common return.

8. The guidewire of claim 1, wherein each of the plurality of electromagnetic microsensors comprises an inner encapsulation and an outer encapsulation.

9. A guidewire assembly comprising:
  a guidewire having:
    a proximal end;
    a distal end with a flexible tip;
    a core member extending between the proximal end and the flexible tip, the core member having a distal tip;
    a plurality of electromagnetic microsensors spaced apart from each other, disposed distal to the core member's distal tip, and embedded within the flexible tip, wherein each of the plurality of electromagnetic microsensors comprises a ferrite core; and
    an outer member forming an outer covering of the guidewire.

10. The guidewire of claim 9, wherein the outer member comprises an outer sleeve comprising a flexible polymer material, a coiled spring, or a coiled wire wrapped around the core member and plurality of electromagnetic microsensors.

11. The guidewire of claim 9, wherein the core member defines a groove near its distal end to better retain the flexible tip on the core member.

12. The guidewire of claim 9, wherein the plurality of electromagnetic microsensors each include a plurality of wire windings wound around the core.

13. The guidewire of claim 12, wherein each electromagnetic microsensor includes a lead wire and a return wire extending from the plurality of wire windings wound around the core.

14. The guidewire of claim 13, wherein each return wire from the plurality of electromagnetic microsensors is connected to a common return.

15. The guidewire of claim 13, wherein the core member includes an opening extending therethrough to allow each lead and return wire from the plurality of electromagnetic microsensors to pass through the opening to the proximal end of guidewire for connection to connectors at the proximal end thereof.

16. The guidewire of claim 9, wherein the flexible tip includes a plurality of tubular members spaced apart from each other and spaced between sections of the outer member, and wherein a wall of the tubular members is thinner than a wall of the outer member.

17. The guidewire of claim 16, wherein the plurality of tubular members are bonded to sections of the outer member with a bond material.

18. The guidewire of claim 17, wherein the plurality of electromagnetic microsensors are mounted within the plurality of tubular members.

19. The guidewire of claim 18, wherein an outer surface of each electromagnetic microsensor is bonded to an inner surface of each tubular member with a bond material.

20. The guidewire of claim 9, wherein the core member is a wire core member.

21. The guidewire of claim 9, wherein the core member is a tubular core member.

22. The guidewire of claim 21, wherein the tubular core member includes grooves that extend through a wall of the tubular core member.

23. A guidewire assembly comprising:
   a guidewire having:
      a proximal end;
      a distal end with a flexible tip;
      a tubular core member;
      a plurality of electromagnetic microsensors that include a ferrite core, wherein the plurality of electromagnetic sensors are spaced apart from each other and mounted within the tubular core member; and
      an outer member forming an outer covering of the guidewire.

24. The guidewire of claim 23, wherein the tubular core member is electrically insulated from the outer member with an insulating layer positioned therebetween.

25. The guidewire of claim 23, wherein each electromagnetic microsensor includes a lead wire and a return wire extending from a plurality of wire windings wound around the ferrite core.

26. The guidewire of claim 25, wherein each return wire from the plurality of electromagnetic microsensors is electrically connected to the tubular core member.

27. The guidewire of claim 23, wherein the tubular core member comprises grooves extending through a wall of the tubular core member.

28. The guidewire of claim 27, wherein the grooves extend only partially around a circumference of the tubular core member.

* * * * *

UNITED STATES PATENT AND TRADEMARK OFFICE
CERTIFICATE OF CORRECTION

PATENT NO. : 8,239,003 B2
APPLICATION NO. : 11/735634
DATED : August 7, 2012
INVENTOR(S) : Samuel Joseph Akins It is certified that error appears in the above-identified patent and that said Letters Patent is hereby corrected as shown below:

In the Specification

In Column 2, line 64, please delete "microsensorors" and replace with --microsensors--.
In Column 3, line 9 and 12, please delete "microsensorors" and replace with --microsensors--.
In Column 4, line 47, please delete "microsensorors" and replace with --microsensors--.
In Column 6, line 5, please delete "microsensorors" and replace with --microsensors--.
In Column 7, line 33, please delete "microsensorors" and replace with --microsensors--.
In Column 9, line 16, please delete "microsensorors" and replace with --microsensors--.
In Column 10, line 45, please delete "microsensorors" and replace with --microsensors--.

Signed and Sealed this
Fifth Day of November, 2013

Teresa Stanek Rea
*Deputy Director of the United States Patent and Trademark Office*